(12) United States Patent
Buan et al.

(10) Patent No.: US 11,819,602 B2
(45) Date of Patent: *Nov. 21, 2023

(54) CHEMICAL PUMP HOUSING FOR NEGATIVE PRESSURE SYSTEM

(71) Applicant: Aatru Medical, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US); Reed Oliver Saunders, Minneapolis, MN (US); Thomas Arthur Tedham, Eden Prairie, MN (US)

(73) Assignee: Aatru Medical, LLC, Cleveland, OH (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/405,315

(22) Filed: Aug. 18, 2021

(65) Prior Publication Data

US 2021/0379271 A1     Dec. 9, 2021

Related U.S. Application Data

(63) Continuation of application No. PCT/US2020/019405, filed on Feb. 24, 2020.

(Continued)

(51) Int. Cl.
*A61M 1/00* (2006.01)
*A61F 3/00* (2006.01)
*A61F 13/00* (2006.01)

(52) U.S. Cl.
CPC ....... *A61M 1/732* (2021.05); *A61F 13/00068* (2013.01); *A61M 1/80* (2021.05);

(Continued)

(58) Field of Classification Search
CPC .......... A61F 13/00068; A61F 13/0216; A61M 1/0003; A61M 1/732; A61M 1/80;

(Continued)

(56) References Cited

U.S. PATENT DOCUMENTS

| 5,439,143 A | 8/1995 | Brown et al. |
| 7,361,184 B2 | 4/2008 | Joshi |

(Continued)

FOREIGN PATENT DOCUMENTS

| WO | 2017075381 | 5/2017 | |
| WO | WO-2017075331 A1 * | 5/2017 | ............. A61F 13/00 |

OTHER PUBLICATIONS

European Search Report filed in EP 20 76 2777 dated Oct. 19, 2022.

(Continued)

*Primary Examiner* — Matthew P Travers
(74) *Attorney, Agent, or Firm* — Rankin, Hill & Clark LLP

(57) ABSTRACT

A chemical pump assembly useful for negative pressure therapy includes a chemical pump housing having an inner chamber, a reactor located within the inner chamber, an opening provided in the chemical pump housing, a first pull tab which extends from the inner chamber to ambient through the opening, and a removable layer connected to the first pull tab. The reactor is configured to react with a selected gas found in air so as to consume the selected gas when exposed to air in the inner chamber. The removable layer shields the reactor from air in the inner chamber atmosphere until the removable layer is removed.

11 Claims, 6 Drawing Sheets

Related U.S. Application Data

(60) Provisional application No. 62/811,698, filed on Feb. 28, 2019.

(52) U.S. Cl.
CPC .............. *A61M 1/962* (2021.05); *A61M 1/984* (2021.05); *A61M 1/964* (2021.05); *A61M 2202/0208* (2013.01); *A61M 2207/00* (2013.01); *A61M 2209/088* (2013.01)

(58) Field of Classification Search
CPC .......... A61M 1/90; A61M 1/94; A61M 1/962; A61M 1/964; A61M 1/984–985; A61M 2207/00; A61M 2202/0208; A61M 2205/0277
See application file for complete search history.

(56) References Cited

U.S. PATENT DOCUMENTS

| | | | |
|---|---|---|---|
| 10,046,095 B1 | 8/2018 | Middaugh et al. | |
| 10,828,202 B1 * | 11/2020 | Buan | A61F 13/0216 |
| 11,083,833 B1 * | 8/2021 | Buan | A61F 13/00068 |
| 2005/0070835 A1 | 3/2005 | Joshi | |
| 2012/0316538 A1 * | 12/2012 | Heiser | A61M 1/60 604/543 |
| 2014/0230817 A1 * | 8/2014 | Richardson | A61M 15/0091 128/203.15 |
| 2017/0119487 A1 | 5/2017 | Binder | |
| 2017/0181894 A1 | 6/2017 | Allen | |
| 2017/0368239 A1 | 12/2017 | Askem | |
| 2018/0207390 A1 * | 7/2018 | Rowland | A61M 15/0035 |
| 2018/0318165 A1 | 11/2018 | Donda | |
| 2022/0241489 A1 * | 8/2022 | Buan | A61M 1/81 |

OTHER PUBLICATIONS

International Search Report filed in PCT/US2020/019405 dated May 14, 2020.

\* cited by examiner

CHEMICAL PUMP HOUSING FOR NEGATIVE PRESSURE SYSTEM

BACKGROUND

Negative pressure therapy is a therapeutic treatment that utilizes negative pressure for skin treatments and restorative purposes. Negative pressure is a term used to describe a pressure that is below normal atmospheric pressure. Negative pressure therapy is utilized for several sites on the skin, such as a wound or an incision. Furthermore, negative pressure therapy is useful to manage wounds with complex healing concerns. Additionally, negative pressure therapy could also be used for cosmetic purposes like removing wrinkles.

Generally, negative pressure therapy is achieved by maintaining a reduced pressure beneath a dressing on a dressing site. A vacuum generation source, such as a pump, applies reduced pressure to the inside of the dressing on the dressing site.

SUMMARY

A chemical pump assembly useful for negative pressure therapy includes a chemical pump housing having an inner chamber, a reactor located within the inner chamber, an opening provided in the chemical pump housing, a first pull tab which extends from the inner chamber to ambient through the opening, and a removable layer connected to the first pull tab. The reactor is configured to react with a selected gas found in air so as to consume the selected gas when exposed to air in the inner chamber. The removable layer shields the reactor from air in the inner chamber until the removable layer is removed.

A method for operating a pump assembly of a negative pressure system, includes providing a fluid connection between a chemical pump housing and a dressing placed over a tissue site. The method further includes pulling a first pull tab, which extends from an inner chamber of the chemical pump housing to ambient through an opening in the chemical pump housing. Pulling the first tab can remove a removable layer to expose a reactor located within the inner chamber to air. The method further includes covering the opening to prevent ingress of air into the inner chamber through the opening.

DETAILED DESCRIPTION

Figure 1:
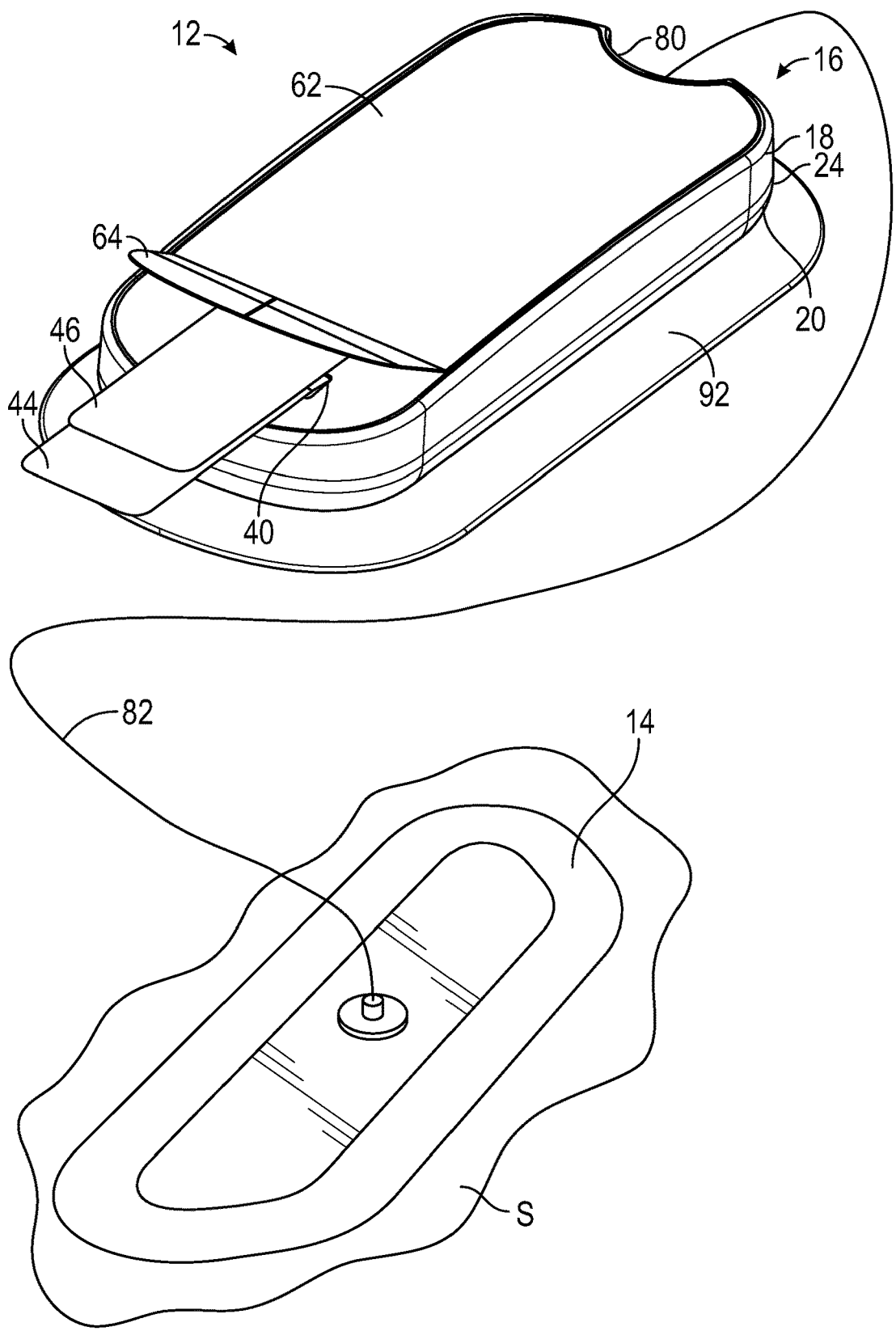
FIG. 1 is a perspective view of a chemical pump assembly.

FIG. 1 depicts a chemical pump assembly 12 useful for negative pressure therapy. Negative pressure described herein is pressure below atmospheric pressure. The chemical pump assembly 12 is configured to connect with a dressing 14 affixed to skin S so as to be in fluid communication with an enclosed volume beneath the dressing 14. An example of the dressing 14 that can be used with the chemical pump assembly 12 is described in U.S. application Ser. No. 16/114813.

The chemical pump assembly 12 generally includes a chemical pump housing 16 including an upper housing 18 and a lower housing 20 that connect to define an inner chamber 22 (FIG. 3) disposed there between. In one embodiment, the upper housing 18 and the lower housing 20 can be constructed as separate elements. When the upper housing 18 and the lower housing 20 are separate elements, the upper housing 18 and the lower housing 20 are joined together, and a seam 24 is formed between the upper housing 18 and the lower housing 20. When the upper housing 18 and the lower housing 20 are joined, an air tight seal is formed between the upper housing 18 and the lower housing 20. In result, no gas can enter or escape the inner chamber 22 of the chemical pump housing 16 through the seam 24. In another embodiment, the upper housing 18 and the lower housing 20 could be integrally formed. Furthermore, the upper housing 18 may include an upper inner wall surface 26 which is only slightly curved and nearly planar, as depicted in FIG. 4. The lower housing 20 may include a lower inner wall 28 offset from the sidewalls of the lower housing 20.

Figure 3:
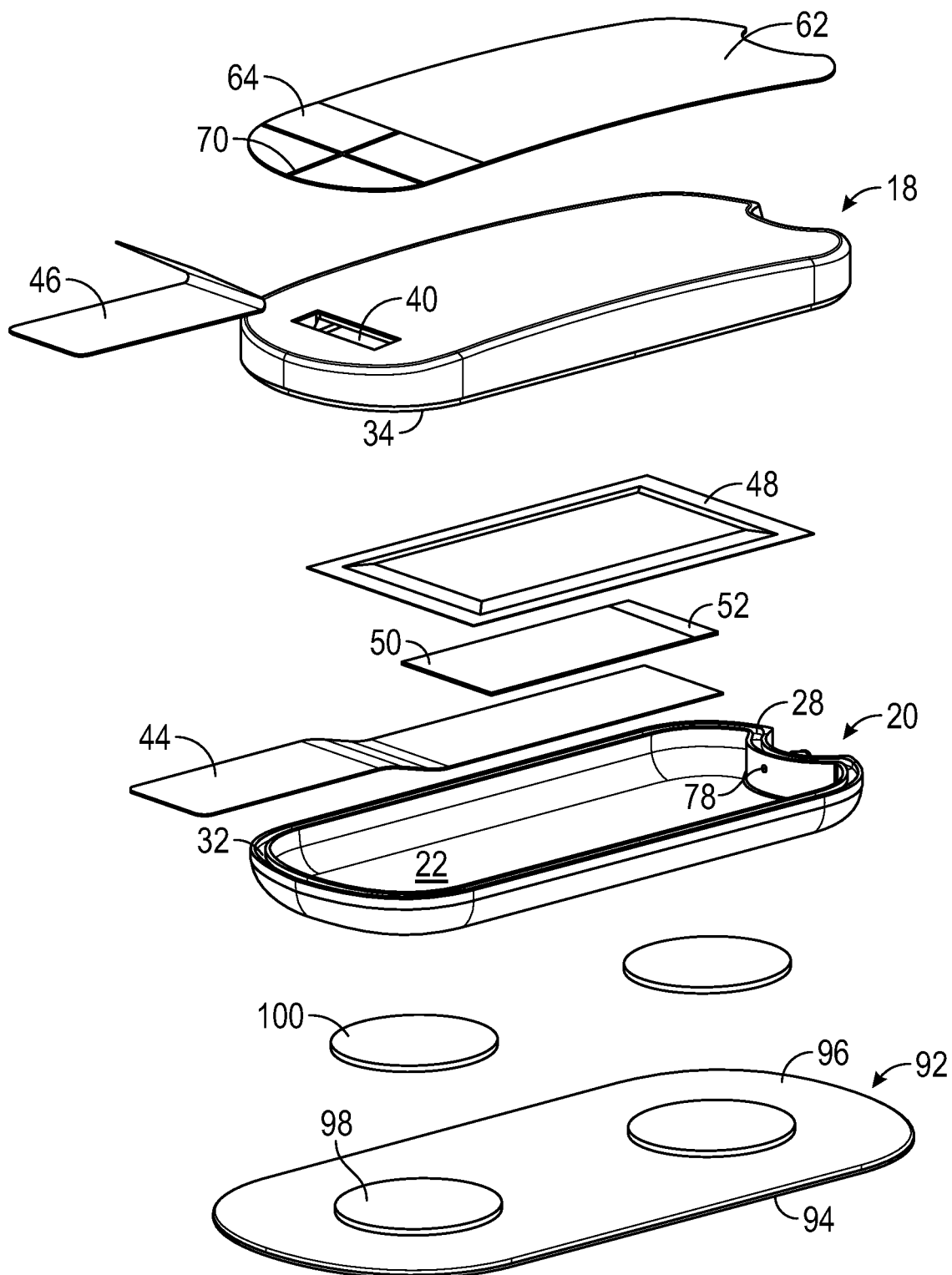
FIG. 3 is a perspective exploded view of the chemical pump assembly.
Figure 4:
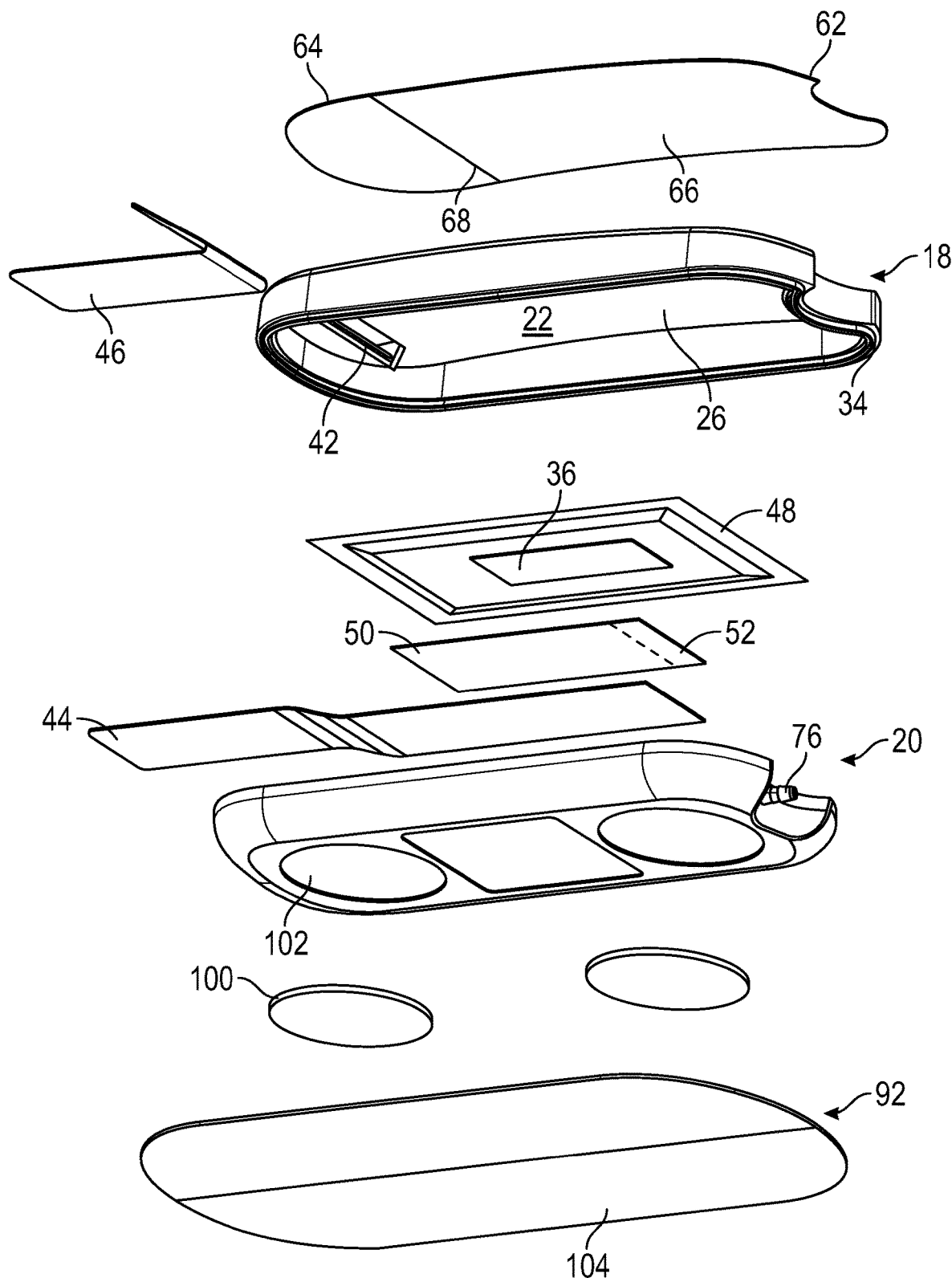
FIG. 4 is another perspective exploded view of the chemical pump assembly.
Figure 5:
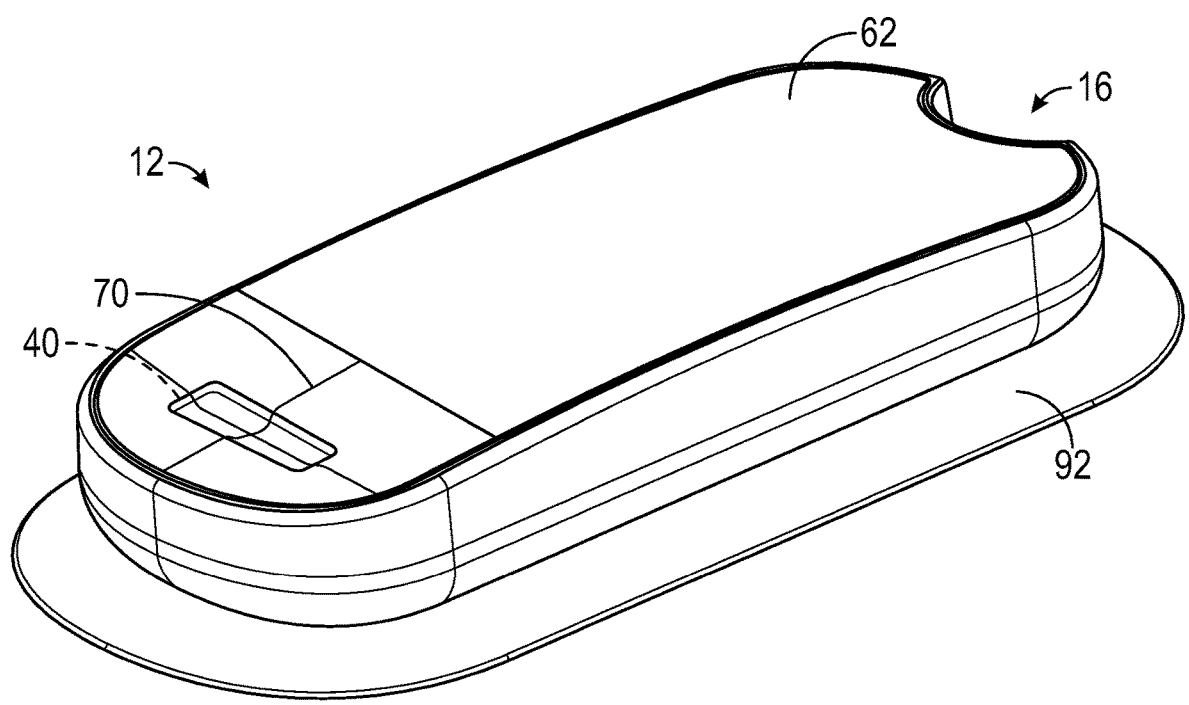
FIG. 5 is a perspective view of the chemical pump assembly after a first pull tab and a second pull tab have been removed.

The lower housing 20 may further include a channel 32, as shown in FIG. 3, disposed around the inner periphery of the lower housing 20. The channel 32 may surround the entire inner periphery of the lower housing 20 or surround only a portion of the inner periphery of the lower housing 20. Furthermore, the channel 32 can be comprised of a single channel or multiple channels. The channel 32 may be disposed between the sidewalls of the lower housing 20 and the lower inner wall 28. On the upper housing 18, a ridge 34 may surround the inner periphery of the upper housing 18, as shown in FIG. 4. The ridge 34 may surround the entire inner periphery of the upper housing 18 or surround only a portion of the inner periphery of the upper housing 18. The ridge 34 can be comprised of a single ridge or multiple ridges. Alternatively, the ridge 34 may be disposed on the lower housing 20, and the channel 32 may be disposed on the upper housing 18.

The ridge 34 is configured to be inserted into the channel 32 when the upper housing 18 and the lower housing 20 are joined. When the ridge 34 is inserted into the channel 32, the upper housing 18 and the lower housing 20 can be welded and the air tight seal is created to prevent gas from passing through the seam 24. The upper housing 18 and the lower housing 20 can connect in other known manners to provide an air tight seal at the seam 24.

The chemical pump assembly 12 further includes a chemical pump 36. The chemical pump 36 is positioned in the inner chamber 22 of the chemical pump housing 16 prior to connecting the upper housing 18 and the lower housing 20. In the illustrated embodiment, the chemical pump 36 in the chemical pump assembly 12 is a reactor configured to react with a selected gas, e.g., oxygen, found in air. Examples of reactors that can be used in the chemical pump assembly 12 are described in US 2014/0109890A1 and PCT/US2016/059364.

An opening 40, which is in the form of an elongate slit in the illustrated embodiment, is disposed on the upper housing 18. The opening 40 is preferably positioned towards a distal side of the upper housing 18. However, the opening 40 can be positioned towards a proximal section of the upper housing 18 as well as elsewhere on the chemical pump housing 16. When not covered, the opening 40 exposes the inner chamber 22 to ambient atmosphere. Adjacent the opening 40, the upper housing 18 can also include a sloped wall 42 that slopes upwardly and toward the distal side of the upper housing 18 from the inner chamber 22 toward the outer surface.

Figure 2:
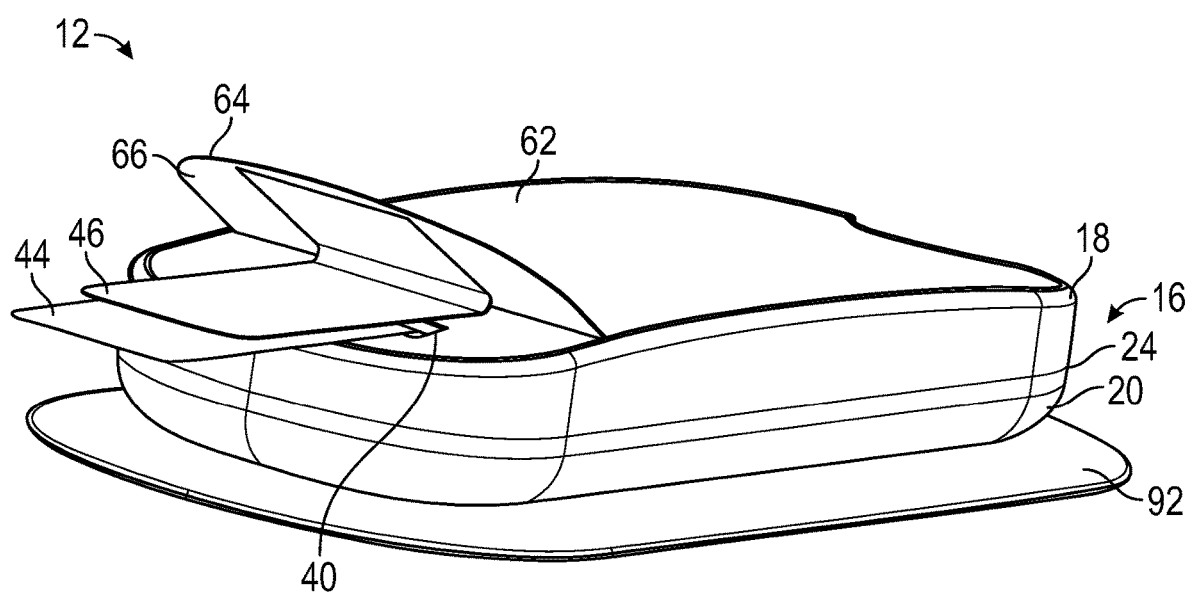
FIG. 2 is another perspective view of the chemical pump assembly.

At least one pull tab extends from the inner chamber 22 to ambient through the opening 40, as shown in FIG. 2. In one embodiment, the at least one pull tab includes a first pull tab 44 and a second pull tab 46. In one embodiment, the first pull tab 44 and the second pull tab 46 are separate elements, whereas, in another embodiment, the first pull tab 44 and the second pull tab 46 could be connected or integral.

With reference to FIGS. 3 and 4, a packet 48 including a removable layer 50 covers the chemical pump 36 so as to prevent the chemical pump 36 from being exposed to ambient atmosphere or air within the inner chamber 22 until after removal of the removable layer 50 from the packet 48. The packet 48 can be a foil packet that is hermetically sealed around the chemical pump 36. The first pull tab 44 extends through the opening 40 and is connected to removable layer 50. The first pull tab 44 can be pulled to remove the first pull tab 44 from the opening 40. When the first pull tab 44 is pulled through the opening 40, the removable layer 50 is removed from the packet 48 and, if desired, from the inner chamber 22 through the opening 40, exposing the chemical pump 36 to ambient atmosphere. After the removal of the removable layer 50, the chemical pump 36 begins to react with a selected gas, e.g., oxygen, in the inner chamber 22. Since the wall 42 is sloped, the first pull tab 44 and the removable layer 50 are removed from the opening 40 with ease. The first pull tab 44 is preferably removed after the chemical pump assembly 12 is connected to the dressing 14. However, the first pull tab 44 can be removed prior to affixing the chemical pump assembly 12 to the dressing 14.

In the illustrated embodiment, the packet 48 is affixed to the upper inner wall surface 26 of the upper housing 18 through an adhesive. The packet 48 could be affixed to another surface, if desired. The removable layer 50 is coated on an upper side (per the orientation shown in FIG. 3) with an adhesive, with the exception of a small section 52 at and end of the removable layer 50 opposite from the opening 40. The upper side of the removable layer being the side facing the packet 48. The first pull tab 44 connects with this small section 52, which lacks the adhesive, and the connection between the first pull tab 44 and the removable layer 50 is limited to the small section 52 in that the first pull tab 44 is free to move with respect to the remainder of the removable layer 50 that carries the adhesive on the upper side and is affixed to the packet 48. As such, when the first pull tab 44 is pulled away from the chemical pump housing 16 through the opening 40, the removable layer 50 rolls over on itself as the removable layer 50 is peeled away from the packet 48.

The chemical pump assembly 12 further includes a cover, an example of which being a thin film 62 described below, for sealing the opening 40 to prevent ingress of air through the opening 40 into the inner chamber 22 after the removable layer 50 has been removed. Other types of covers, e.g., films not already connected with the chemical pump housing 16, can also be employed.

The second pull tab 46 cooperates with the thin film 62, which is placed over and adhered to a portion of the top surface of the upper housing 18. The thin film 62 includes a flap 64 and, as depicted in FIG. 2, the opening 40 is disposed underneath the flap 64. The second pull tab 46 is connected to a release layer 66 provided on a bottom surface of the thin film 62. The release layer 66 covers an adhesive (not visible in FIG. 2) on the bottom surface of the thin film 62. With reference to FIG. 4, a slit 68 is provided in the release layer 66 so that one section of the release layer 66 is removed exposing the adhesive prior to affixing the thin film 62 to the top surface of the upper housing 18, while the portion of the release layer 66 beneath the flap 64 can remain. When the second pull tab 46 is pulled, the second pull tab 46 disconnects the release layer 66 from the flap 64 and the adhesive disposed on the bottom surface of the flap 64 is exposed. The flap 64 is then moved towards the upper housing 18 to cover the remainder of the top surface of the upper housing 18 and thus also covers the opening 40. In result, the inner chamber 22 is no longer exposed to ambient atmosphere via the opening 40. In the illustrated embodiment, the thin film 62 is metallized to prevent the ingress of air into the inner chamber 22 when the inner chamber 22 is at negative pressure. When the thin film 62 covers the opening 40, the chemical pump 36 reacts with the selected gas found in the enclosed volume under the dressing, and if already connected to the dressing via a hose 82 (shown schematically in FIG. 1 and in phantom in FIG. 6) creates a closed system. Reduced pressure is therefore developed within the enclosed volume. When the inner chamber 22 is under negative pressure, the thin film 62 is drawn in through the opening 40 toward the inner chamber 22. As such, the thin film 62 cooperating with the opening 40 can provide an indication to the user that the inner chamber 22 is under negative pressure. Indicia 70, e.g. lines, a cross or the like, can also be provided on the thin film 62 in the vicinity of the opening 40 to provide further indication of negative pressure.

The chemical pump housing 16 further includes a hose fitting 76, which in the illustrated embodiment is a barbed fitting to secure fixation of the hose 82 to the hose fitting 76. The hose fitting 76 is tubular and includes a passage 78 in communication with the inner chamber 22. In one embodiment, the hose fitting 76 is disposed on the opposite side of the chemical pump housing 16 as the opening 40. The hose fitting 76 may be disposed on a concave section 80 of the chemical pump housing 16; however, the hose fitting 76 may be disposed on any surface of the chemical pump housing 16. The concave section 80 can be alternatively disposed on any surface of the chemical pump housing 16. The hose 82 (schematically depicted) attaches to the hose fitting 76 to connect the chemical pump assembly 12 to the dressing 14.

With reference back to FIG. 1, the chemical pump assembly 12 can further include an attachment pad 92 disposed underneath and connected with the lower housing 20. The attachment pad 92 includes a lower side 94 and an upper side 96. Fasteners, e.g. hook and loop fasteners, 98 may be disposed on the upper side 96 of the attachment pad 92 for connection with hook and loop fasteners 100 received inside recesses 102 provided in a bottom surface of the lower housing 20 to affix the attachment pad 92 to the chemical pump housing 16. The attachment pad 92 may be larger than the chemical pump housing 16. The lower side 94 of the attachment pad 92 is configured to attach to a surface, e.g. a gown or clothing worn by a patient, or the patient. The attachment pad 92 may include an adhesive layer disposed on the lower side 94. A removable attachment pad release liner 104 can be disposed on the adhesive. The removable attachment pad release liner is removed to expose the adhesive.

A method for operating the chemical pump assembly 12 will be described hereinafter. At least one dressing 14 can be placed over a tissue site. The chemical pump assembly 12 can then connect to the at least one dressing 14 via the hose 82. When the chemical pump assembly 12 is connected to the at least one dressing 14, the inner chamber 22 of the chemical pump assembly 12 is in fluid communication with the enclosed volume defined by the dressing 14. Either pull tab 44 or 46 can be pulled. When the first pull tab 44 is pulled through the opening 40 the removable layer 50 is removed from the packet 48. In result, the chemical pump 36 in the chemical pump housing 16 is exposed to ambient atmosphere as well as air in the inner chamber 22 and begins to react with a selected gas. The second pull tab 46 is pulled to remove the release layer 56 provided on a bottom surface of the flap 54 to expose adhesive on the bottom surface. The flap 54 is then brought toward the upper housing 18 to cover the opening 40 with the thin film 62. As a result, the inner chamber 22 is no longer exposed to ambient atmosphere. The reactor then reacts with the selected gas in the inner chamber 22 and the enclosed volume beneath the dressing 14 and applies reduced pressure at the tissue site.

Figure 6:
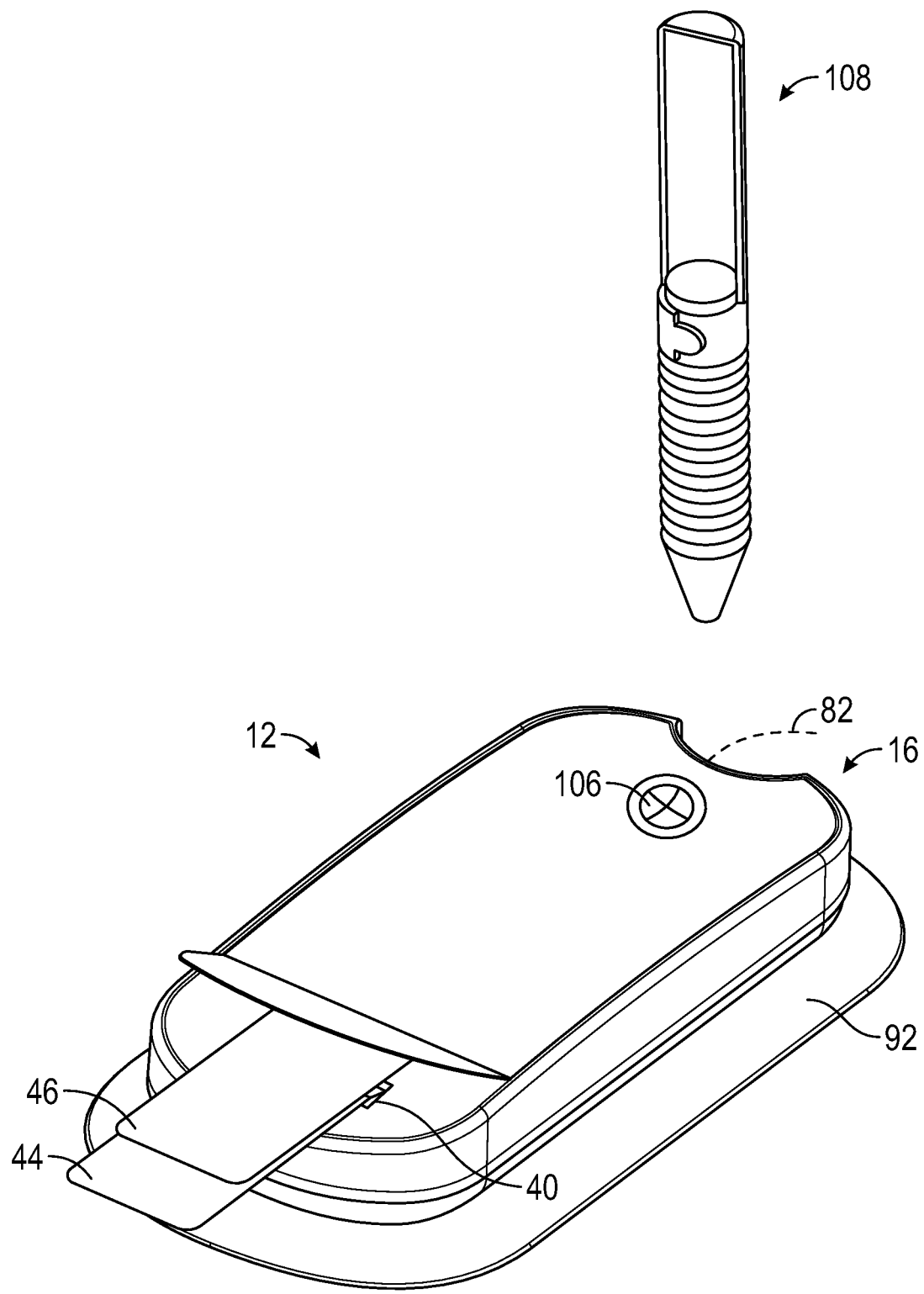
FIG. 6 is a perspective view of a chemical pump assembly including a valve.

FIG. 6 depicts the chemical pump housing 16 including a valve, which can be a bidirectional valve 106. Note, the chemical pump 36 and packet 48 may need to be reduced in size or the size of the chemical pump housing 16 may need to be enlarged to accommodate the bidirectional valve 106. The bidirectional valve 106 may be similar in construction to the valve described in U.S. Pat. No. 5,439,143. The bidirectional valve 106 can be configured such that (1) when the air pressure external to the bidirectional valve 106 is below the air (or gas pressure) of the inner chamber 22 the bidirectional valve 106 opens and air is allowed to be drawn from the inner chamber 22 through the bidirectional valve 106, (2) when the ambient air pressure is more than a predetermined differential (e.g., 200 mmHg) greater than the air (or gas pressure) of the inner chamber 22 the bidirectional valve 106 opens and air is allowed to enter the inner chamber 22 through the bidirectional valve 106, and (3) in other instances the bidirectional valve 106 remains closed so as to prevent air from entering or exiting the inner chamber 22 through the bidirectional valve 106. It is in this third state in which the inner chamber 22, and therefore the enclosed volume beneath the dressing, is in a therapeutic range, e.g., between −50 mmHg to −200 mmHg offset from ambient atmosphere (e.g., absolute pressure of 560 to 710 mmHg at sea level). If desired, a mechanical pump assembly 108, which is more particularly described in PCT/US19/12298, can be inserted into the bidirectional valve 106, thus opening the valve, and activated to provide negative pressure to the enclosed volume beneath the dressing 14 when the chemical pump assembly 12 is connected with the dressing via the hose 82. Also, conventional wall suction pumps, sometimes referred to as "wall suction," can also connect with the bidirectional valve 106, thus opening the valve to provide negative pressure to the enclosed volume beneath the dressing 14 when the chemical pump assembly 12 is connected with the dressing via the hose 82.

Instead of the bidirectional valve 106, two one-way valves could also be employed. One of the one-way valves can be configured such that when the air pressure external to the one-way valve is below the air (or gas pressure) of the inner chamber 22 the one-way valve opens and gas is allowed to be drawn from the inner chamber 22 through the one-way valve. The other one-way valve can be configured such that when the ambient air pressure is more than a predetermined differential (e.g., 200 mmHg) greater than the air (or gas pressure) of the inner chamber 22 this one-way valve opens and air is allowed to enter the inner chamber 22 through the one-way valve. Both one-way valves would remain closed when the inner chamber 22 is in a therapeutic range, e.g., between −50 mmHg to −200 mmHg offset from ambient atmosphere (absolute pressure of 560 to 710 mmHg at sea level). The mechanical pump assembly 108, wall suction or similar mechanical suction device could cooperate with the one-way valve that allows air to enter the inner chamber 22.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of assembling a chemical pump assembly useful for negative pressure therapy, the method comprising:
   providing a packet and a chemical pump, which is configured to react with and consume oxygen, the packet covering the chemical pump, wherein the packet includes a removable layer and is configured to prevent the chemical pump from being exposed to air until after removal of the removable layer from the packet;
   providing a first pull tab connected with the removable layer; and
   locating the packet within an inner chamber of a chemical pump housing and extending the first pull tab from the inner chamber through an opening provided in the chemical pump housing to ambient atmosphere.

2. The method of claim 1, further comprising:
   affixing a cover to an outer surface of the chemical pump housing, the cover being configured to seal the opening to prevent ingress of air through the opening into the inner chamber after the removable layer has been removed.

3. The method of claim 2, further comprising:
   connecting a second pull tab to a release layer covering adhesive provided on the cover.

4. The method of claim 2, wherein affixing the cover to the outer surface of the chemical pump housing further comprises:
   providing indicia on the cover, wherein the indicia is configured to provide an indication to a user that the inner chamber is under negative pressure when the thin film cover is adhered to the outer surface over the opening.

5. The method of claim 1, wherein locating the packet within the inner chamber of the chemical pump housing further includes:
   affixing the packet to an upper inner wall surface of an upper housing of the chemical pump housing.

6. The method of claim 5, wherein locating the packet within the inner chamber of the chemical pump housing further includes:
   affixing the packet to the upper inner wall surface of the upper housing of the chemical pump housing prior to joining a lower housing to the upper housing.

7. The method of claim 1, further comprising:
   providing at least one valve on the chemical pump housing in fluid communication with the inner chamber and ambient atmosphere, the at least one valve being configured such that (1) when air pressure external to the at least one valve is below gas pressure of the inner chamber the at least one valve opens and air is drawn from the inner chamber through the at least one valve, (2) when ambient air pressure is more than a predetermined differential greater than the gas pressure of the inner chamber the at least one valve opens and air enters the inner chamber through the at least one valve, and (3) in other instances the at least one valve remains closed so as to prevent air from entering or exiting the inner chamber through the at least one valve.

8. The method of claim 7, further comprising:
providing a mechanical pump assembly that is connectable to the chemical pump assembly at the at least one valve.

9. The method of claim 1, wherein locating the packet within the inner chamber of the chemical pump housing further includes:
extending the first pull tab through the opening over a sloped wall adjacent the opening that slopes upwardly and toward an outer surface of the chemical pump housing.

10. A method of assembling a chemical pump assembly useful for negative pressure therapy, the method comprising:
providing a packet and a chemical pump, which is configured to react with and consume oxygen, the packet covering the chemical pump, wherein the packet includes a removable layer and is configured to prevent the chemical pump from being exposed to air until after removal of the removable layer from the packet;
providing a first pull tab connected with the removable layer;
locating the packet within an inner chamber of a chemical pump housing and extending the first pull tab through an opening in the chemical pump housing to ambient atmosphere; and
connecting a hose to a hose fitting provided on the chemical pump housing.

11. The method of claim 10, further comprising:
connecting the hose to a dressing.

* * * * *